US005853423A

United States Patent [19]
McGregor et al.

[11] Patent Number: 5,853,423
[45] Date of Patent: Dec. 29, 1998

[54] PROCESS FOR THE MANUFACTURE OF SUTURE NEEDLES AND NEEDLES PRODUCED THEREBY

[75] Inventors: Walter McGregor, Flemington; Semyon Shchervinsky, Whitehouse Station, both of N.J.

[73] Assignee: Ethicon, Inc., Somerville, N.J.

[21] Appl. No.: 139,251

[22] Filed: Oct. 20, 1993

[51] Int. Cl.$^6$ .............................. A61B 17/04; B21G 3/18
[52] U.S. Cl. ................................................ 606/222; 163/5
[58] Field of Search .................................. 606/222–226; 163/5; 72/337, 339, 317

[56] References Cited

U.S. PATENT DOCUMENTS

| | | | |
|---|---|---|---|
| 383,733 | 5/1888 | Jenkins | 606/226 |
| 1,591,897 | 7/1926 | Morton | 606/223 |
| 1,592,535 | 7/1926 | Morton | 606/223 |
| 1,636,615 | 7/1927 | Quint | 606/223 |
| 2,811,157 | 10/1957 | Kurtz et al. | 606/223 |
| 3,038,475 | 6/1962 | Orcutt | 606/223 |
| 3,160,157 | 12/1964 | Chisman | 606/223 |
| 3,238,942 | 3/1966 | Lincoff | 606/223 |
| 4,197,643 | 4/1980 | Burstone et al. | |
| 4,404,830 | 9/1983 | Koch | 72/339 |
| 4,513,747 | 4/1985 | Smith | |
| 4,660,559 | 4/1987 | McGregor et al. | |
| 4,672,734 | 6/1987 | Kawada et al. | |
| 4,799,484 | 1/1989 | Smith et al. | |
| 4,828,547 | 5/1989 | Sahi et al. | |
| 4,883,469 | 11/1989 | Glazier | |
| 4,883,471 | 11/1989 | Braginetz et al. | |
| 4,905,695 | 3/1990 | Bendel et al. | |
| 5,100,432 | 3/1992 | Matsutani | |
| 5,123,910 | 6/1992 | McIntosh | |

FOREIGN PATENT DOCUMENTS

| 0670199 | 4/1952 | United Kingdom | 606/223 |
|---|---|---|---|

OTHER PUBLICATIONS

Abidin et al., Biomechanics of Curved Surgical Needle Bending, J. Biomed. Mater. Res. Appl. Biomaterials, vol. 23, No. A1, 129–143, (1989).

Bendel et al., Ophthalmic Needles, *Ophthalmology*, vol. 93, No. 9, (Sep. 1986).

McClung et al., Biomechanical Performance of Ophthalmic Surgical Needles, *Ophthalmology*, vol. 99, No. 2 (Feb. 1992).

Pavolvich, Lucas J., et al. A Synthetic Membrane for Testing Needle Penetration, *Journal of Applied Biomaterials*, vol. 4, 157–160 (1993).

Bendel, Lee P., et al., Tensile & Bend Relationship of Several Surgical Needle Materials, *Journal of Appl. Biomaterials*, vol. 4, 161–167 (1993).

*Primary Examiner*—Gary Jackson
*Attorney, Agent, or Firm*—Emil Richard Skula

[57] ABSTRACT

A process for the manufacture of suture needles and, more particularly, a process for enhancing the physical strength of the suture needles through an expedient cold-working or cold-forming procedure. Also disclosed is the provision of a novel and physically strengthened suture needle, particularly a surgical suture needle possessing a curvilinear configuration wherein the cross-sectional configuration of the needle is cold-formed into varying shapes in order to produce a needle having superior physical characteristics and strengths imparted thereto through the inventive process. The needles are essentially cold formed, and which process includes the aspect of imparting to straight metal rods which are preferably constituted from stainless steel, manufacturing steps which include sharpening one end of rod severed segments so as to form the needle tip, thereafter curving the needle with the metal still being in a relatively ductile state, and subjecting the needle to a cold forming process, such as through the intermediary of pressure die molds or stamping, to produce varying cross-sectional shapes along the length of the needle.

7 Claims, 2 Drawing Sheets

PROCESS FOR THE MANUFACTURE OF SUTURE NEEDLES AND NEEDLES PRODUCED THEREBY

BACKGROUND OF THE INVENTION

1. Field of the Invention

The present invention relates to a process for the manufacture of suture needles and, more particularly, relates to a process for enhancing the physical strength of the suture needles through an expedient and novel cold-working or cold-forming procedure. Moreover, the invention also relates to the provision of a novel and physically strengthened suture needle, particularly a surgical suture needle possessing a curvilinear configuration wherein the cross-sectional configuration of the needle is cold-formed into varying shapes in order to produce a needle having superior physical characteristics and strengths imparted thereto through the inventive process.

2. Discussion of the Prior Art

Currently, various types of processes are known and widely utilized in the technology relating to the manufacturing of suture needles, and particularly needles which are adapted to have sutures fastened thereto by means of various types of procedures so as to meet the stringent requirements of the suture needle-manufacturing technology for so-called armed sutures. Generally, suture needles are formed from suitable metals, especially such as different types of stainless steel, wherein the needles are produced from thin rod material which is ordinarily cut into appropriate lengths commensurate with the length of the intended suture needle. The severed length of rod usually has one end thereof formed into a needle point, or has a needle point attached to that end, and has appropriate cross-sectional dimensions imparted thereto, such as through stamping, laser processing, grinding or the like, and thereafter curved into the finished curvilinear configuration prior to the attaching thereto of a suture. Sutures are then attached to the end of the formed suture needle opposite the needle point through either the application of suitable adhesives, or by being placed into a groove formed at that end of the needle and thereafter the suture-needle assembly swaged to formulate an appropriate permanent fastening between the needle end and the contiguous end of the suture, thereby forming a so-called armed suture arrangement.

In some instances, the metallic material of the suture needle is also subjected to a heat treatment in order to complete the needle manufacturing process.

Among various processes directed to the forming of suture needles are those disclosed in Kawada et al. U.S. Pat. No. 4,672,734. In that instance, various shapes are imparted to the suture needle prior to the curving thereof into its final configuration. Such shapes may include the stamping into the needle surface of various cross-sectional configurations along the length of the needle which is to be formed; for example, including the forming of grooves or rolling of the material into a tubular shape to enable the insertion therein of suture ends for subsequent attachment to the needle. Thereupon, the cross-sectionally shaped needle is subjected to bending in order to impart the desired curvature thereto and to provide the needle with its finished configuration.

The above-mentioned U.S. patent, although providing an improvement over the existing state-of-the-art in the manufacture of suture needles, still does not produce a suture needle construction possessing an enhanced physical strength in comparison with the previous state-of-the-technology, in that it essentially requires the needle to be curved subsequent to imparting the various cross-sectional shapes thereto, which quite often, causes the inherently resilient nature of the metal employed for the suture needle, such as high-quality stainless steel to cause the needle to resiliently "spring back" to some degree or in effect, to "uncurve". This will at times produce a needle construction and curvature which is not in strict conformance with the intended final dimensions and curvature of the surgical needle, while concurrently rendering the process relatively expensive and cumbersome. This imposes serious problems on being able to implement a satisfactory quality control over the suture needles, leading to numerous rejects and rendering the manufacturing process not only laborious and cumbersome but frequently highly uneconomical.

SUMMARY OF THE INVENTION

The present invention overcomes the disadvantages and drawbacks encountered in the prior art with regard to the manufacture of suture needles, in that the novel and unique process produces suture needles which are easily manufactured, are able to maintain their tolerances and finished shapes, and are of an enhanced physical strength in contrast with those produced in prior art processes particularly as discussed in and represented by the above-identified U.S. Pat. No. 4,672,734.

In order to improve upon the quality and physical strength of suture needles of surgical quality in comparison with those being produced pursuant to prior art processes, the present invention contemplates the provision of a manufacturing process in which the needles are essentially cold formed, and which include the steps of imparting to straight metal rods which are preferably constituted from stainless steel, manufacturing steps which include sharpening one end of rod severed segments so as to form the needle tip, thereafter curving the needle with the metal still being in a relatively ductile state, and subjecting the needle to a cold forming process, such as through the intermediary of pressure die molds or stamping, to produce varying cross-sectional shapes along the length of the needle. This cold forming, in essence, a cold-working process is implemented to the needle in order to form the various shapes along the length thereof subsequent to imparting the curvature to the suture needle, enhances the physical strength thereof; potentially up to 15 to 20% over presently employed processes for manufacturing suture needles.

Furthermore, pursuant to the inventive process there are produced improved suture needles which, through a simple cold-forming step in providing specified variable cross-sectional dimensions and configurations along the length of the previously curved suture needle, clearly and unambiguously enhance the physical strength of the stainless steel from which the suture needle is constituted, to a considerable degree, potentially up to 15 to 20% over currently manufactured needles, as a result of the cold-working or cold-forming step implemented subsequent to forming the curvature, and which also eliminates the tendency of the material to "uncurve". This aspect; in effect, not only imparts an enhanced degree of physical strength to the cold-formed suture needle, but also concurrently enables a more precise control to be exerted over the curvature thereof, inasmuch as the cold-forming will inhibit the needle from reverting towards a straightened configuration, and thereby enable a more precise shape to be imparted thereto.

It is, accordingly, a primary object of the present invention to provide an improved process for the manufacture of suture needles so as to impart an enhanced degree of physical strength to the needles.

Another object of the present invention resides in the provision of a novel cold-forming process for forming suture needles and which, subsequent to imparting the curvature to the needle, contemplates cold forming the material to impart specified variable cross-sectional configurations along the length of the suture needle, so as to enhance the physical characteristics and strength of the suture needle material.

Yet another object of the present invention is to provide a suture needle formed by the inventive cold-forming process, resulting in an enhanced strength of the suture needle.

BRIEF DESCRIPTION OF THE DRAWINGS

Reference may now be had to the following detailed description of an exemplary embodiment of the invention, taken in conjunction with the accompanying drawings; in which:

FIG. 3 illustrates, on an enlarged scale, a cross-sectional view through the suture needle taken along line 3—3 in FIG. 2a.

DETAILED DESCRIPTION OF A PREFERRED EMBODIMENT

Figure 1:
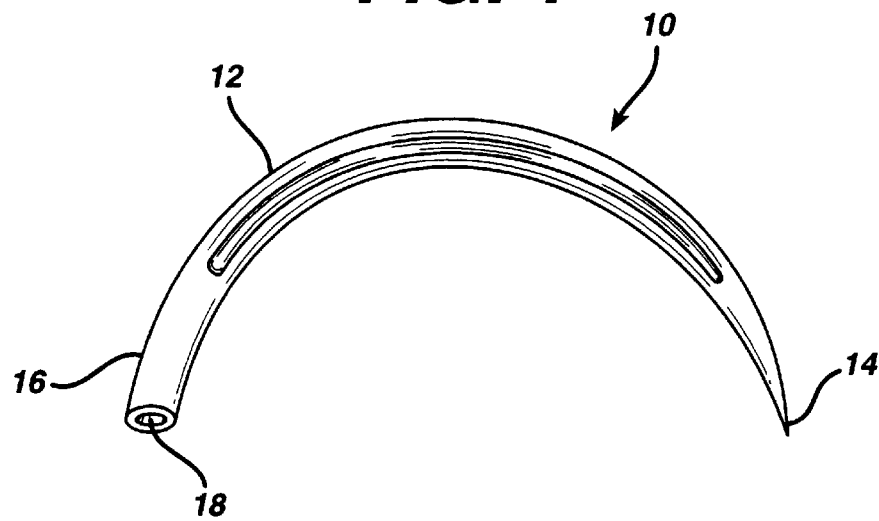
FIG. 1 illustrates a perspective view of a curved suture needle produced in accordance with the cold-forming process of the invention.

Referring now more specifically to the drawings, in FIG. 1 there is illustrated a typical suture needle 10 which includes a body portion 12 and a sharp tip 14, the latter of which may be either integrally formed with the body portion 12 or attached thereto as a separate component.

In essence, the suture needle 10 is produced from a rod-shaped member constituted of a metallic material, such as stainless steel, and preferably a Type 420 or 455 surgical-quality stainless steel alloy, as is well known in the technology of manufacturing surgical instruments. At one end 16 of the suture needle provision is made; for instance, through the formation of a suitable groove 18 or the like, enabling the receipt and positioning therein of the end of a suture (not shown) which may then be fastened to the suture needle 10, such as by either the application of an adhesive or through a swaging operation, as is well known in the technology of producing armed sutures.

The suture needle 10 is imparted a curvilinear configuration by being bent along substantially a major portion of length thereof, extending from the needle tip 14 towards the body portion 12 and end 16 for attaching a suture.

Normally, the suture needle is formed from a segment of stainless steel rod which may have a sharp needle tip ground or machined at one end thereof distant from the suture-attaching end. Thereafter the needle may be imparted a specified cross-sectional shape through a suitable stamping or die molding process, possibly while still in a heated state, so as to enable the attachment of a suture at one end thereof opposite the end having the needle tip; and finally the entire structure is bent into the required curvature and treated in order to produce the finished suture needle. This particular sequence in the manufacturing steps, although presently widely employed in industry, is subject to definite limitations and drawbacks, inasmuch as the generally hot working of the material and the bending of the suture needle into the required curvilinear configuration subsequent to forming the cross-sectional shape of the needle frequently leads to the needle "uncurving"; in essence, a springing back of the still somewhat resilient stainless steel forming the needle. Consequently, at times, the finished needle may not possess the required curvature and dimensions required by the specific intended applications thereof, leading to considerable quantities of needles being rejected during the manufacturing cycle. Additionally, the manufacture of suture needles in that manner does not at all times impart the desired physical strength to the relatively delicate suture needles, so as to again potentially generate problems for a surgeon or medical practitioner in the use of such surgically-employed needles with thereto attached sutures.

As illustrated in FIGS. 2a through 2d and FIGS. 3 and 4 of the drawings, the present invention improves upon the foregoing process of manufacture, in providing a suture needle 10 of enhanced physical strength, and the manufacture of which enables the needles to be manufactured within extremely precise tolerances and parameters without encountering the drawback of any potential "uncurving" of the needle taking place, while simultaneously, rendering the entire suture needle manufacturing process inexpensive and simple to implement through the use of conventional cold-forming or cold-working apparatus.

In essence, an initially straight rod member 20, which is constituted from a suitable stainless steel material; for instance, Type 420 or 455 alloy, and having a requisite basically circular cross-section which is commensurate in size with the intended suture needle structure, is cut from a continuous rod to produce the rod segment 20 having a first end 22 and an opposite or second end 24.

Figure 2A:
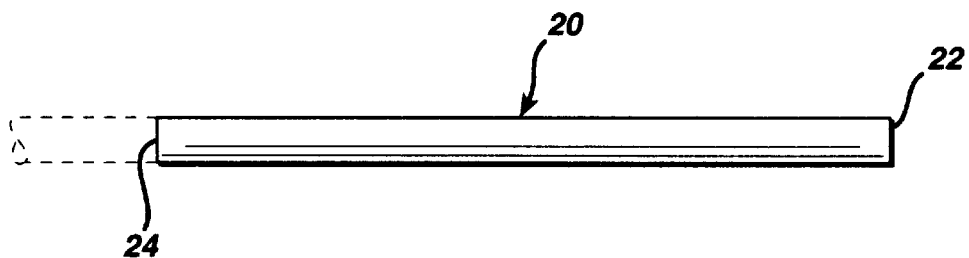
FIGS. 2a through 2d, respectively, illustrate successive steps in the cold-forming process in manufacturing the suture needle of FIG. 1.
Figure 2B:
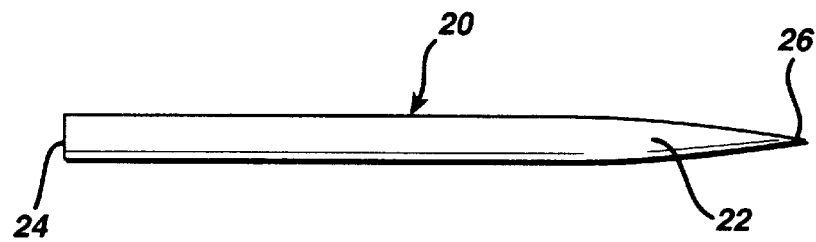

Thereafter, as shown in FIG. 2b, a suitable sharp needle tip 26 may be formed at the end 22, such as by either laser machining, grinding or electromechanical grinding, as is known in the art; or alternatively, attached to the end as a separate component of the needle. Thereafter, the rod segment 20 with the sharp needle tip thereon at the end 22 is bent into the required curvilinear configuration, as in FIG. 1, so as to produce a curved portion 28 extending from the sharp needle tip 26 towards the remaining body portion 30 proximate the end 24 to which suture is intended to be subsequently attached so as to form an armed suture.

Figure 2C:
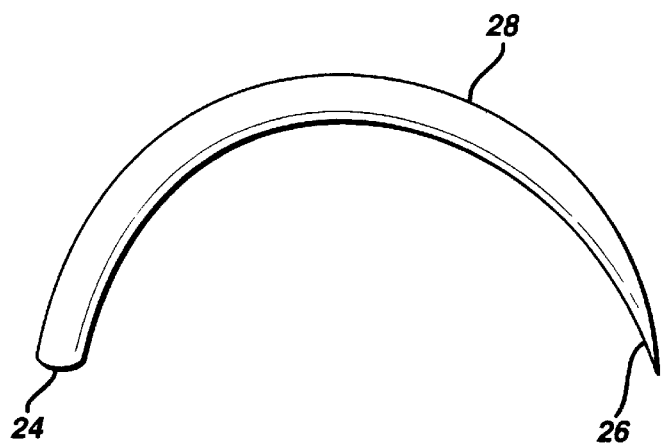
Figure 2D:
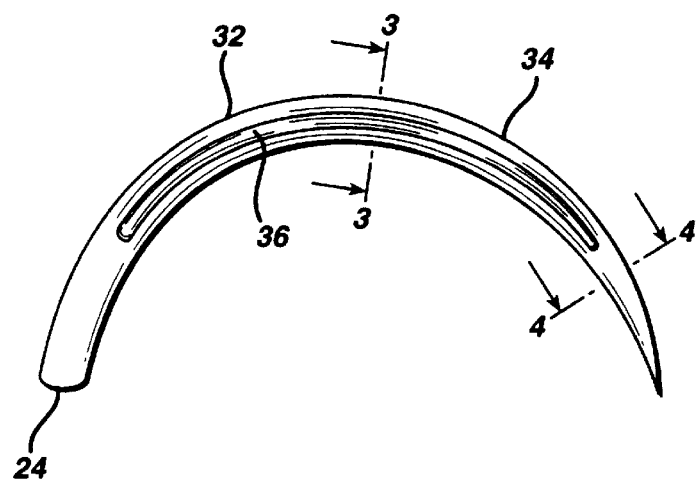
Figure 3:
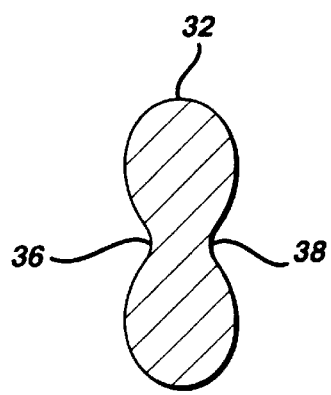
Figure 4:
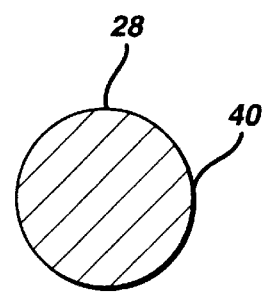
FIG. 4 illustrates, in a view similar to FIG. 3 a cross-sectional view through the suture needle, taken along line 4—4 in FIG. 2d.

Thereafter, as shown in FIG. 2d, the curved structure portion 32 of the suture needle, as shown in FIG. 2c, is subjected to either a stamping process or cold-formed between suitable die mold halves; in effect, cold-formed or cold-worked so as to impart various cross-sectional configurations to the suture needle along the length thereof, as may be desired. For instance, a needle portion extending from close to location 34 towards the end 24 to which the suture is adapted to be attached, may be cold-formed to assume a shape as shown in FIG. 3 wherein indentations or grooves 36 and 38 are cold-formed on opposite sides of the suture needle, whereas the section of the suture needle portion 32 between location 34 and the needle tip 26, may possess a circular cross-section 40 as shown in FIG. 4 of the drawings. Naturally, other cross-sectional configurations, as desired, may, of course, be contemplated as falling within the scope of the present cold-forming process such as ovals, ellipsoids, etc. The cold-forming of the suture needle after curving thereof pursuant to the foregoing process imparts a higher degree of physical strength to the suture needle, possibly by up to a 15 to 20% higher strength than needles which have been heretofore produced through a heat-treating process, and as also currently employed in the technology.

Alternatively, another cold-working method in addition to that set forth hereinabove may consist in cold-rolling the material of the suture needle, with this procedure being imparted over the length of the needle in order to increase the physical strength thereof.

From the foregoing, it quite readily becomes apparent that the inventive process presents a simple method of cold working or cold-forming suture needles to imbue them with superior physical strengths in comparison with needles currently being conventionally produced in this technology, while enabling the process to be carried out with generally conventional equipment in a simple, expedient and highly economical manner.

While there has been shown and described what is considered to be a preferred embodiment of the invention, it will, of course, be understood that various modifications and changes in form or detail could readily be made without departing from the spirit of the invention. It is, therefore, intended that the invention be not limited to the exact form and detail herein shown and described, nor to anything less than the whole of the invention herein disclosed as hereinafter claimed.

What is claimed is:

1. A process for producing a suture needle from a rod element constituted of metallic material, comprising the steps of:

a) cutting said metallic rod element to a predetermined length;

b) bending said cut rod element into a specified curvilinear configuration;

c) and cold-working said curved rod element to form specific cross-sectional shapes and dimensions along the length thereof.

2. A process as claimed in claim 1, comprising the step of forming a sharp needle tip at one end of said suture needle preceding the step of bending said rod element into said curvilinear configuration.

3. A process as claimed in claim 2, comprising forming an end of said suture needle distant from said first end into a shape adapted for the attachment of a suture to said needle.

4. A process as claimed in claim 1, wherein said cold-working comprises the step of cold-forming said needle by the application of pressure in a die mold to produce said specific cross-sectional shapes and dimensions.

5. A process as claimed in claim 1, wherein said cold-working comprises the step of cold-forming said needle by stamping said specific cross-sectional shapes and dimensions into said curved rod element.

6. A process as claimed in claim 1, wherein said specific cross-sectional shapes comprise depressions and grooves cold-formed in the sides of the curved suture needle.

7. A process as claimed in claim 1, wherein the metallic material of said rod element comprises stainless steel.

* * * * *